United States Patent [19]

Buckson

[11] 4,203,673
[45] May 20, 1980

[54] METHOD AND APPARATUS FOR OPTICALLY INSPECTING CYLINDRICAL ARTICLES

[75] Inventor: Gerald I. Buckson, Wilmington, Del.

[73] Assignee: E. I. Du Pont de Nemours and Company, Wilmington, Del.

[21] Appl. No.: 872,499

[22] Filed: Jan. 26, 1978

[51] Int. Cl.$^2$ ............................................. G01N 21/48
[52] U.S. Cl. .................................... 356/446; 209/587; 250/224; 250/578
[58] Field of Search ................. 356/73, 167, 209, 210, 356/237, 160, 199, 200, 163, 380, 386; 429–431, 445, 446; 250/560, 223 B, 224, 578; 209/517, 518, 587

[56] References Cited

U.S. PATENT DOCUMENTS

| | | |
|---|---|---|
| 3,746,575 | 7/1973 | Arnaudin, Jr. et al. .......... 356/237 X |
| 3,822,945 | 7/1974 | Robinson et al. ................ 356/237 X |
| 3,870,890 | 3/1975 | Binks et al. ............................ 250/560 |
| 4,058,737 | 11/1977 | Takahashi et al. .............. 356/197 X |

Primary Examiner—John K. Corbin
Assistant Examiner—Bruce Y. Arnold

[57] ABSTRACT

The inspection of a cylindrical article is accomplished by scanning the surface of the article in a plane transverse to its longitudinal axis with a light beam sequentially reflected from mirrors spaced about the periphery of the article. Light that is reflected or scattered from the article's surface is detected by sensors which are symmetrically positioned on either side of the scanning plane. Intensity variations and time variations of the sensor signals thus produced are processed to extract information concerning the article's surface uniformity, cross sectional shape, longitudinal shape and length as the article is moved along its longitudinal axis through the inspection plane.

An apparatus is also described for effecting such a method. The apparatus uses a rotating polygonal mirror scanner, a plurality of fixed mirrors positioned in the scanning plane peripherally around the article to be inspected and annular sensors positioned fore and aft of the scanning plane through which the articles pass. This arrangement results in a plurality, n+1, of subscans around the article for each facet scan of the polygonal mirror. The article is moved along its longitudinal axis through the inspection plane such that the successive scans progress along the longitudinal axis of the article in a helical manner.

14 Claims, 7 Drawing Figures

METHOD AND APPARATUS FOR OPTICALLY INSPECTING CYLINDRICAL ARTICLES

BACKGROUND OF THE INVENTION

This invention relates to a method and apparatus for optically inspecting the peripheral surfaces of cylindrical article(s). The articles may be discrete parts or continuous, such as cables or tubing.

Many approaches have been made in an effort to inspect three-dimensional parts. Such inspection, to be thorough, is relatively difficult and expensive to perform. One of the major problems encountered in such inspection is that the parts and the inspection sensor must somehow be indexed, rotated or otherwise moved in relation to one another in order to accomplish 100% inspection of the surface. This becomes increasingly difficult by conventional means as the speed of the inspection process is increased.

Among the various inspection systems that have been employed to inspect cylindrical articles have been those which optically illuminate the entire peripheral surface for visual inspection. See, for example, U.S. Pat. No. 2,607,267. Others effect such complete illumination but rely on photoresponsive materials instead of the human eye to elicit an output signal. Visual inspection is inadequate for obvious reasons—it is too slow and is subject to human judgmental error. The other approaches generally are not specific.

Following these early efforts, people have more recently used light beams such as laser beams to scan the surface of the cylindrical articles. To effect a complete inspection of the entire surface, the article is rotated about its longitudinal axis while the object is translated or the beam is traversed in a direction parallel to the axis.

In one system, disclosed in U.S. Pat. No. 3,834,822, for example, a cylindrical object to be inspected for surface defects is rotated about its axis and a collimated laser beam is axially scanned across the object's surface in a plane normal to the surface. The detectors, while symmetrically arranged on each side of the scanning plane, are of conventional design and detect light diffusely reflected in a limited angular range. Moreover, since there is no axial movement of the object being inspected, the inspection rate is significantly slowed and fewer articles can be inspected in a given time interval.

In regard to scanning techniques employed for moving objects, the major problem encountered has been the inability to detect reflected light with adequate responsivity to obtain a generally error-free, meaningful signal. A particular problem arises in inspecting cylindrical shells, such as shotgun shells, where it is necessary not only to detect surface flaws, but also anomalies in their geometrical configurations. The problem encountered here is the high speed with which the shells are passed through the inspection apparatus.

SUMMARY OF THE INVENTION

This invention provides an improved method and apparatus which permits unimpeded, passage of moving cylindrical articles while at the same time permitting effective scan coverage of the articles' peripheral surfaces and detection of non-specularly reflected incident radiation. The method and apparatus may be used to inspect either discrete or continuous articles.

According to the method, an elongated generally cylindrical article has its peripheral surface optically inspected by successively scanning the surface transversely of the member's axis with beams of light directed from each of a plurality of different circumferential locations, sensing the intensity of light non-specularly reflected from the surface of the member; varying the position of the scanning along the longitudinal axis of the member, and comparing variations in the reflected light intensity.

In a preferred embodiment, the reflected light is sensed simultaneously at different axial locations symmetrically placed on either side of the scanning position. In this manner, the reflected light can be detected at a relatively small angle to the article longitudinal axis and at all radical positions about the periphery. The sensing is by annularly shaped sensors to maximize the resulting signal strength.

Apparatus for inspecting the surface or geometric characteristics of an elongated generally cylindrical article with a beam of radiation includes: a rotatable mirror drum of regular polygonal cross-section, means to direct the beam onto the drum for successively scanning the beam across said member in a plane transverse to the longitudinal axis of the cylindrical member, a plurality of stationary specularly reflecting surfaces disposed in said plane at different circumferential positions about said axis, each for reflecting said beam in said plane across said article's surface from a different radial location, first annular sensing means positioned parallel to said plane, contiguous thereto, and about the longitudinal axis for sensing radiation from said beam non-specularly reflected from said article's surface, and means for effecting relative movement along said axis between said scanning plane and said article.

In a preferred embodiment, the cylindrical article is moved through the inspecting apparatus and a second annular sensing means is symmetrically positioned contiguous and parallel to but on the opposite side of said scanning plane from said first annular sensing means.

The apparatus described is capable of inspecting substantially all of the peripheral surface area of cylindrical articles moving at high translational rates of speed and producing a highly accurate surface defect signal.

BRIEF DESCRIPTION OF THE DRAWINGS

Further advantages and features of this invention will become apparent upon consideration of the drawings, wherein.

DETAILED DESCRIPTION OF THE PREFERRED EMBODIMENTS

The method and apparatus herein described are specifically adapted for, but not limited to, the inspection at high speeds of generally cylindrical bodies, such as shotshells, for a variety of flaws including surface irregularities, overall body-shape distortions and dimensional disparities. Into the surface irregularity categories fall scratches, occasional holes or blemishes, and tears. The body-shape distortions include geometric anomalies such as oval-cross-sections and bowed bodies, sometimes referred to as "bananas." Each of these surface or shape features produces a distinctive optical effect which is sensed and electronically processed.

Any single one, number, or combination of these flaws can be sensed in a given shell body. Inspection normally takes place at high rates of speed, i.e., 600 units per minute, which places severe requirements on the means for effecting relative movement, in order to provide the necessary positioning and spacing of the shells during the successive optical scans, as well as on any signalprocessing electronics and associated computer means. For the sake of simplicity and clarity of illustration, the method and apparatus will be described in the environment of a shotshell inspection system. It is understood, however, that this invention is capable of inspecting any generally cylindrically shaped articles or body(s) of either discrete or continuous length. Such bodies include those polygonal in cross-section.

According to the method of this invention, the cylindrical article(s) are passed axially (the axis of a cylinder is its axis of revolution which is usually its longitudinal axis) through an inspection zone. In this inspection zone plural beams of radiation, preferably monochromatic coherent radiation such as that provided by a laser, are swept or scanned across the cylindrical article in a plane which is generally transverse to the axis of the article. Radiation that is non-specularly reflected from the surface of the article, as the scanning beam sweeps across the article surface, is sensed preferably, as will be described hereinafter, with ring-like or annular sensors placed axially on either side of the scanning plane. In this manner surface irregularities which cause an increase in the nonspecularly reflected radiation cause discernible signals that are sensed similarly by the two sensors as the scanning beams encounter and leave the edges of the article. Pulses are created that will vary in amplitude, width and time position. By comparing successive pulses, variations in pulse width will indicate imperfections in the roundness of the articles. Likewise, variations in the time position of the pulses will indicate that the articles are not properly aligned axially, i.e., they may be bananashaped or tilted. The number of scansions is indicative of article length. Appropriate control means may be used with any transport system to accept or reject the various articles according to varying desired criteria as will be described.

In an alternative method, the inspection zone may be moved along the axis of a stationary article to effect the inspection. It is most desirable, when inspecting a large number of rapidly moving discrete articles, that the articles pass through a stationary inspection zone.

Figure 1:
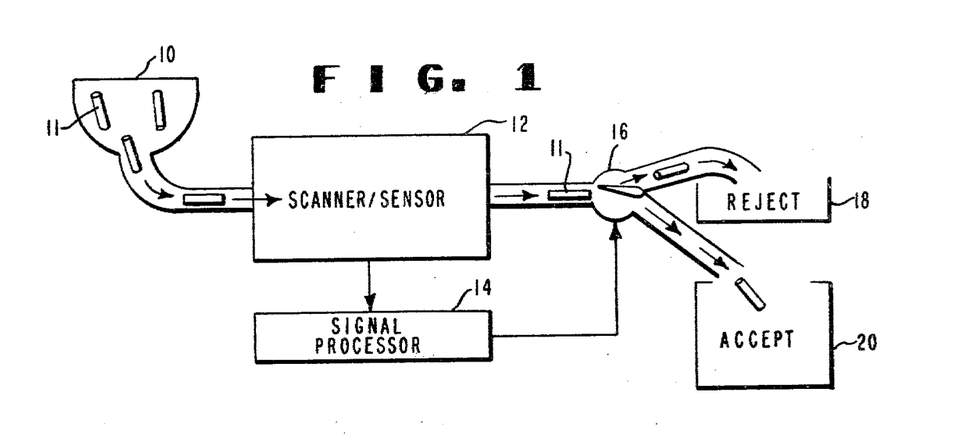
FIG. 1 is a general functional layout of an inspection system for cylindrical articles with which this invention is useful.

Referring to FIG. 1 in the drawings, there may be seen a typical inspection system of the type with which this invention finds use. In this inspection system shotshells 11 are gravity fed in an end-to-end fashion, down a grooved (not shown) slide from an elevated hopper or bowl 10 in a scanner/sensor 12. The scanner/sensor 12, which preferably is constructed as will be described hereinafter in accordance with this invention, may, if it is in the horizontal position such as depicted in FIG. 1, include an additional means as will be described in conjunction with FIG. 5 for positively moving the shells through an inspection zone (FIG. 5) in the scanner/sensor 12. Raw optical inspection signals resulting from the scanning beam in the scanner/sensor 12 are generated and transmitted to an appropriate signal processor 14, which will be described hereinafter in connection with FIG. 6. The scanner/sensor 12 and signal processor 14 generate and process the inspection signal and in accordance with certain criteria provide an output control signal which is passed to a reject gate 16. In cases where a particular shell 11 is indicated to be beyond predetermined tolerance limits for diameter, length, straightness, or severity or number of defects, the reject gate 16 is actuated in proper time sequence so as to direct the individual shells 11 to a reject hopper 18. If the shells are within tolerance they are allowed to pass to an accept hopper 20.

Figure 2:
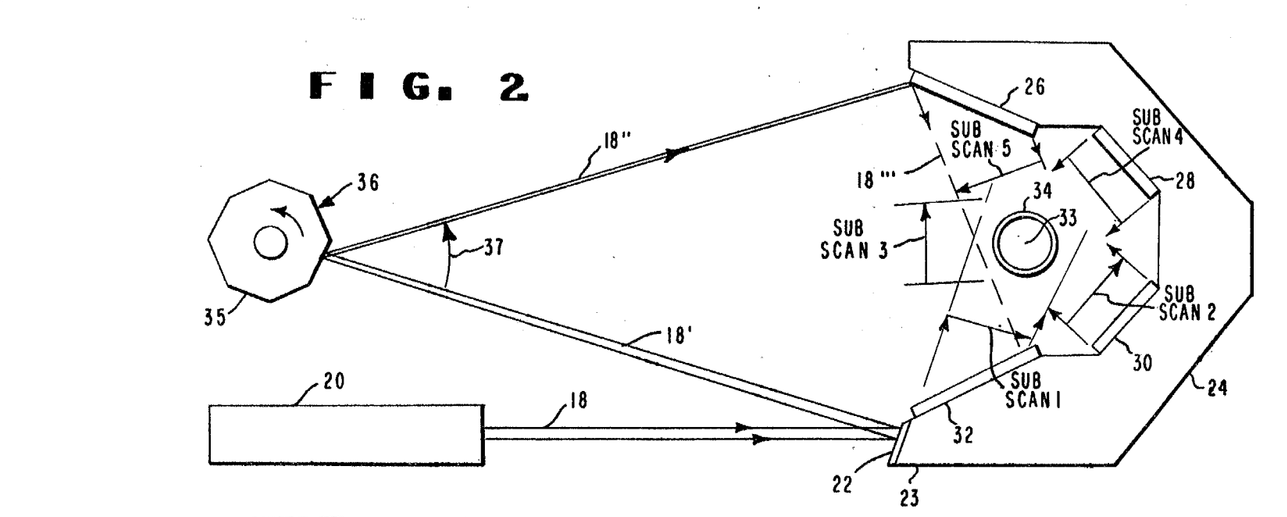
FIG. 2 is a diagrammatic layout of the optical portion of the scanning apparatus which effects circumferential scans about the periphery of cylindrical articles.
Figure 3:
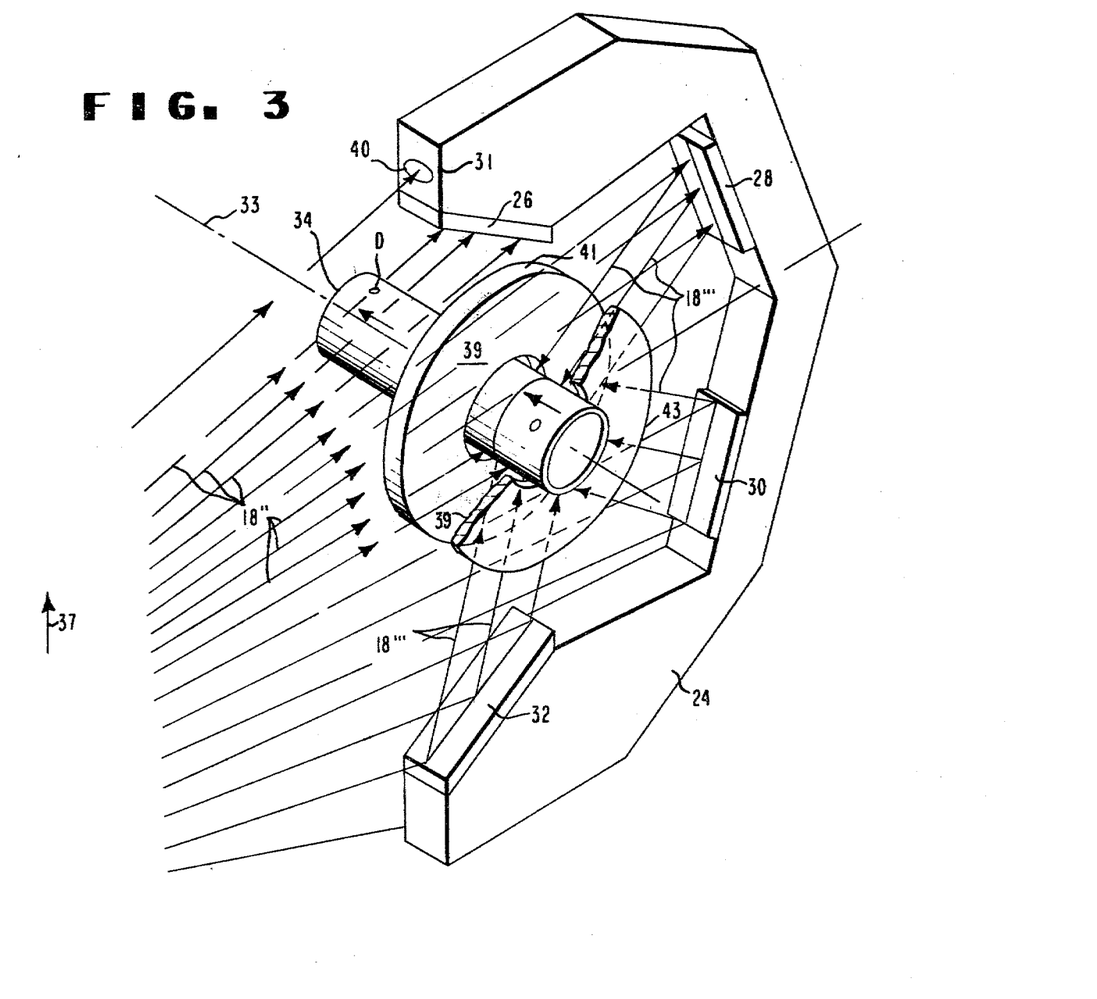
FIG. 3 is a pictorial illustration of a scanning beam sweeping a cylindrical article passing through the inspection system of this invention.
Figure 4:
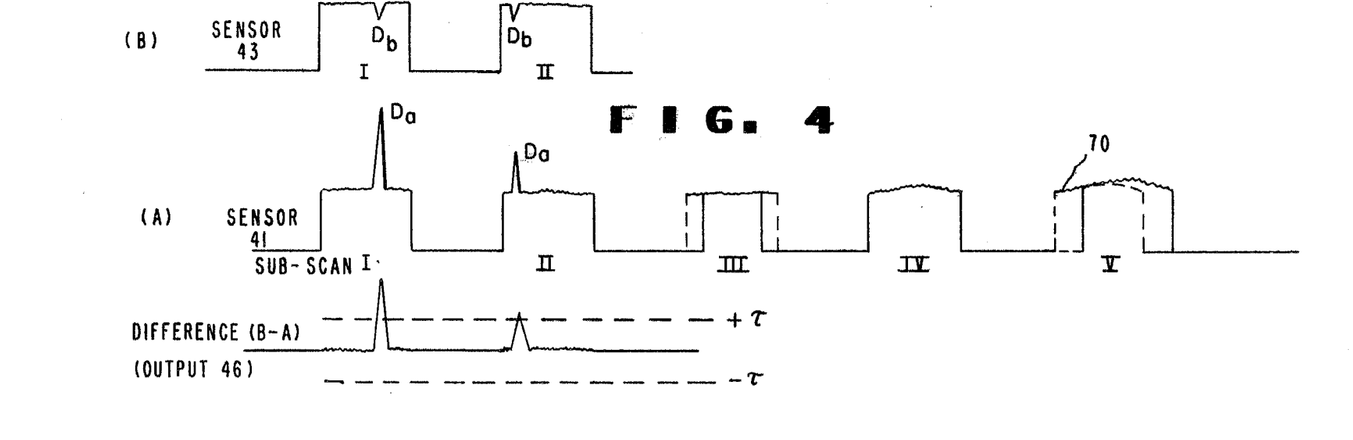
FIG. 4 are waveforms depicting various types of defects in a typical cylindrical article that may be detected by the dual detectors.

The optical inspection apparatus of this invention may be more easily understood with particular reference to FIGS. 2, 3 and 4. FIG. 2 shows a plan view of the components which lie in the inspection zone. They include a source of coherent radiation, such as a helium neon (He Ne) laser 20, capable of providing a collimated beam of electromagnetic radiation or light 18. The collimated beam 18 is directed to a front-surface mirror 22 which may be positioned on one tip 23 of a C-shaped bracket 24. A plurality (in this case 4) of planar, specular reflecting surfaces or mirrors 26, 28, 30 and 32, respectively, are disposed in fixed, spaced apart equiangular relationship coaxially about an axis 33. This axis 33 is the same axis along which the cylindrical objects or shell bodies to be inspected are passed. A shell body 34 is exemplary of these objects; the shell body being shown in cross-section.

The beam 18 after being reflected from the mirror 22 is directed to the surface of a multi-faceted, reflecting polygonal drum 36. The drum 36 is driven by a scan motor (not shown). The reflected beam 18', upon striking the rotating polygon, is caused to sweep or scan along the angle depicted by the arrow 37 in a scanning plane transverse to, preferably perpendicular to the axis 33. Thus the light beams 18" reflected from each successive mirror face of the drum 36 traverses the entire bracket 24 and strikes each mirror 32, 30, 28 and 26 in succession as well as traversing any articles such as shell body 34 in its path.

Each of the mirrors 26, 28, 30 and 32 is properly angled such that as the light is reflected from each mirror face in succession, it forms subscan beams 18''' which scan most of the region in which the shell body 34 is located. These portions of the scan are designated subscan 1, subscan 2, subscan 4 and subscan 5; subscan 3 being effected directly by the beam 18" from the rotating drum 36. It is thus seen that each of the five subscans overlaps with at least one other subscan in 180° segments around the shell body 34, sweeping the shell body in a transverse helical, circumferential line having a width equal to the diameter of the beams 18"; 18'''.

Figure 7:
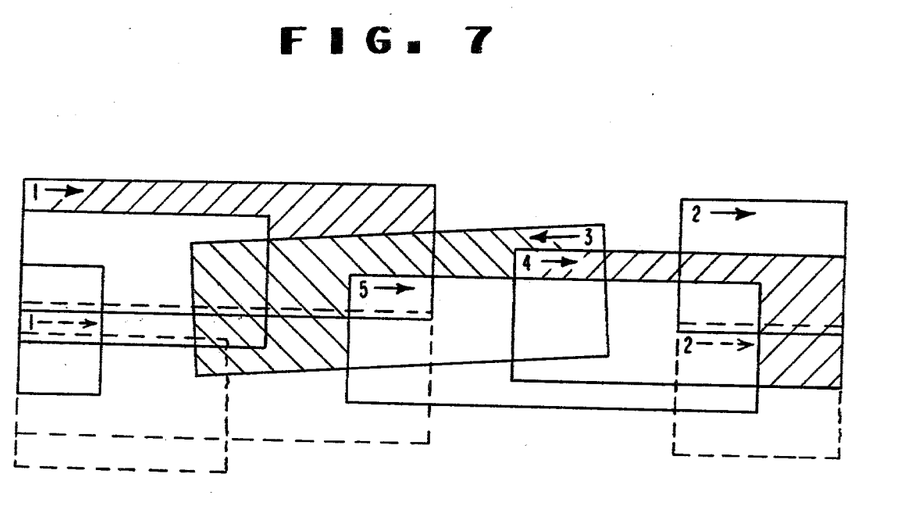
FIG. 7 is a developed view of an article, illustrating a scanning pattern traced by an inspecting light beam.

This overlay is shown detailed in the sketch of FIG. 7. In short each subscan passes through a substantially equal arc which is greater than that necessary to cover the entire diameter of the articles being inspected. In this manner, the time periods of beam contact with the articles are interspersed with periods of disjunction.

The staggered helical scans of the incident beam across the surfaces of the articles are more clearly visualized with reference to FIG. 7, which is an elongated, developed view of a portion of the cylindrical surface of an article, such as a shot-shell. This diagram shows the use of a scanning beam having a width somewhat greater than the spacing between successive sweeps in order to assure complete coverage of the entire surface.

In a typical case, the drum 36 (FIG. 2) may have 16 equiangularly spaced facets 35 and may be rotated at 4270 revolutions per minute (rpm). Under these conditions the sweep frequency would be 1139 Hz, each sweep generating the five subscans noted. Thus, if it is desired to inspect 10 articles, such as shot-shells, per second, each 7.62 cm long with a 2.54 cm gap between shells, the required translatory velocity of the shells would be 101.6 cm per second. At the sweep frequency of 1,139 per second, the total part length covered by each sweep, which includes the five subscans, 1 to 5, would amount to only 0.0892 cm.

This length is depicted in FIG. 7 in greatly enlarged scale by the vertical distance between the beginning and ending scan points. Within each sweep of the beam 18", the five individual subscans, 1-5, overlap accurately, each covering substantially more than one-fifth of the circumference of the shell 34. Subscans 1, 2, 4 and 5 travel from left to right across the cylindrical surface (in the drawing) while subscan 3 (being directly from the rotating mirror 35) scans from right to left (in the drawing). There is a slight step while the part travels between successive scans. In the example, given an effective beam diameter of 0.0127 cm and a total sweep length of 0.0089 cm, it will be seen that the successive sweeps (and their subscans) overlap considerably so that every portion of the part surfaces is inspected more than once. The second scansion of five subscans is depicted by the dashed lines. It will also be observed that the length of the individual parts can be determined accurately by electronically counting and recording the total number of subscans of the light crossing each part.

Light is reflected predominantly in a diffused manner from a shot shell body 34 although there is always some specular reflection. Stated in another manner, the distribution of reflected light surrounding the immediate vicinity of the shell body 34 is approximately Lambertian in nature. In accordance with this invention the non-specularly reflected radiation or light from the shell body is detected using the apparatus depicted particularly in FIG. 3. This apparatus comprises two substantially symmetrically placed annular sensors 41, 43 oriented in parallel contiguous planes, normal to the axis of the shell body, thus permitting the articles to be inspected (in this case the shot shells) to pass through the annulus of the sensors 41, 43. This arrangement defines a concentric dark-field inspection zone so that both forward and backscattered light reflected within a given angle measured from the axis 33 will be directed to and impinge on the photosensitive surfaces 39 of the sensors 41 and 43. These annular sensors may be silicon solid-state PIN diode photodetectors. In the particular application, the silicon photodetectors typically are used in a backbiased mode so as to obtain the desired linearity and frequency response. Of course, any other suitable well-known sensor of this type may be used as well.

Figure 6:
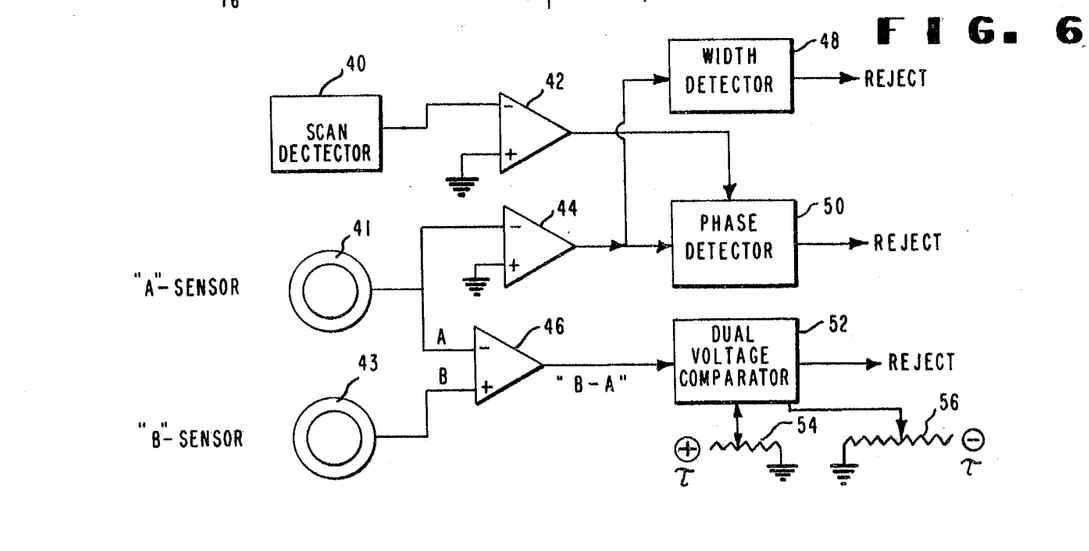
FIG. 6 is a block diagram of a typical electronic processing system that may be used for processing the detected signals of this invention.

The scattered light impinging on the active area 39 of the sensors 41, 43 generates an electrical signal which is supplied through leads (not shown) to electronic circuitry for amplification and processing (FIG. 6). It is thus apparent that the optical sensing arrangement facilitates high-speed inspection as the articles (shot-shells) move axially through the inspection zone (the region defined by the sensors 41, 43) not only due to a relatively high signal-to-noise ratio realized by the unique placement of the sensors, but also as described earlier, substantially greater than 100% inspection coverage of the article surface. To facilitate synchronizing the electronic processing with the sweep occurrence, a scan detect signal is useful. For this purpose scan detector 40 is positioned in the tip 31 (the upper tip in the drawing of FIG. 3) of the bracket 24. This detector may be any suitable solid state sensor, preferably a photo diode, and is electrically coupled to the processing circuitry depicted in FIG. 6. The angles at which the mirrors 26, 28, 30, 32 are positioned may be simply designated by the formula $L = 2\pi/(N+1)$ where N is the number of reflecting surfaces, i.e., for five subscans across the article, four mirrors are employed. In this case where N equals 4 the angular spacing between the mirrors is 72°.

The wave form depicted in FIG. 4 represents a series of five typical signals corresponding to the five subscans that are generated during each scansion of a facet 36. These signals are designated I through V, corresponding to each of the five subscans 1-5. For each subscan, the outputs of the two sensors 41 and 43 are shown as a difference. For the sake of simplicity of illustration, the occurence of many typical defects are depicted in the figure, although in common normal practice the probability that all of these defects would occur in a single scan sequence is extremely low. It is apparent that since the apparatus has inherent redundancy, a given defect "D" (FIG. 3) may be detected in more than one subscansion. Assume for example that a shot-shell 34 (FIG. 3) has the particular discrete surface defect D such as a gouge, scratch, ripple, or some other inhomogeneity in the material. When the scanning beam strikes this flaw D, distinct changes in the pattern of the scattered light impinging on the active area of the sensors 41, 43 occur. Typically these changes in the pattern result in one of the sensors receiving more, and the other proportionately less of the scattered light as the incident scan beam transits the flaw area. The abrupt changes in the amount of radiant energy typically incident on the sensors' active surface during a subscan produce similarly abrupt changes in their electrical outputs. Peaks "$D_a$", depicted in subscans I and II of FIG. 4 illustrate such changes in the output of sensor 41. Here the flaw has momentarily scattered more of the scan beam's energy towards the "A" sensor 41. At the same time less energy is momentarily scattered in "B" sensor's, 43, direction, resulting in a momentary loss in its signal (peaks $D_b$ in subscans I and II).

Signals from either of the two sensors 41 or 43 may be processed individually, or in combination by suitable detection circuitry as depicted in FIG. 6 to extract these signal changes, compare them to limits, and generate a rejection signal if warranted which in turn is applied to operate the reject mechanism 16 (FIG. 1) at the proper point in time to remove the flawed part and pass it to the reject hopper 18. The signal processor circuitry 14 (FIG. 1) which processes the signals from the sensors 41, 43, may include any suitable computer-aided or conventional logic system for detecting the various defects.

An oval or out-of-tolerance diameter in a given shell will be manifested by a pulse of a shorter or longer time duration than normal as depicted by the pedestal output of the sensor 41 (also designated A) for subscan III. On the other hand, a bowed or banana shaped shell will be detected by an early or late appearing signal, although possibly having a correct width, such as depicted by pedestal V. In this case the normal time of occurrence of the pedestal is depicted by the dotted lines 70, whereas the actual pedestal would be noted as late in its normal time for occurrence. Shell length may be determined from the total number of subscans collected from a shell as mentioned earlier. In this connection it should be noted that lateral stability of the shells in moving along axis 33 of the inspection zone is a highly desirable requirement. For example, if the shell is not properly axially aligned, or for that matter, if displaced from its axial position as it moves through the inspection zone, an erroneous rendition of the banana-type defect will probably be indicated, although some minor deviations from the axis may be corrected by appropriate computer processing in accordance with well-known techniques.

Although it is preferred that the signals derived from the sensors 41 and 43 be converted to digital form and processed by a computer with appropriate software to detect deviations in amplitude, pulse width and pulse position, a hardwired analog digital system that may be employed for this purpose is depicted in FIG. 6. This system includes integrated instrument amplifiers 42, 44 and 46 which may be of the conventional, fixed gain high input impedance or operational amplifier type. In this instance the signal from the scan detector 40 is coupled to the negative input of the amplifier 42. The output signal from "A" sensor 41 is connected to the negative inputs of amplifiers 44 and 46, whereas the output from the "B" sensor 43 is coupled to the positive input of amplifier 46, the positive inputs of amplifiers 42 and 44 being connected to ground.

The outputs of the first and second amplifiers 42 and 44 are connected to respective inputs of a phase detector 50. This phase detector may for example incorporate a succession of one-shot multivibrators which will generate maximum and minimum occurrence times based on the scan detector reference time. These are the times during which each of the five subscan signals should occur. If the pedestals from the five subscan signals occurs within these times, they are within acceptable tolerance limits. Any one of the five subscan signals starting or ending outside of these tolerance limits provides a basis for generating a reject signal. This corresponds to the mistiming depicted by the location of pedestal V in FIG. 4.

Similarly, the output of the second amplifier 44 is also connected to a width detector 48. This width detector 48 may include a series of one-shot multivibrators which are adjusted to provide a series of maximum and minimum pulse widths to compare with each of the five subscan signals. Thus, whenever the time durations of the five subscan signals differ, i.e., the actual received subscan pedestal width is greater than or less than the reference pulse widths, a reject signal is generated to actuate the reject gate 16 (FIG. 1).

Finally, the difference amplifier 46 provides an output signal comprising the difference in amplitudes of the two sensor (41 and 43) signals A and B. This difference signal "B-A" is connected to the input of the dual voltage comparator 52. Thus this comparator will produce a digital defect signal whenever the difference between the two sensor (41 and 43) signals exceed either the positive threshold voltage, $+p$, or the negative, $-p$, as set by the adjustable potentiometers 54 and 56 of FIG. 6. This digital defect signal is again applied with suitable delay to the reject gate 16 of FIG. 1.

In alternative embodiments of the invention, the transport system may be that described in the copending, application filed concurrently herewith by Erwin Reitter, Ser. No. 872,498, and for convenience is depicted diagrammatically in FIG. 5. This is a positive action system which is capable of precisely directing the several articles to be inspected through the inspection zone along the axis 33 (FIGS. 2 and 3), here designated "Z". It receives the articles to be inspected, in this case shot-shell casings, by gravity feed from hopper 10 (FIG. 1) and feeds these parts longitudinally along the fixed, preferably vertical feed axis "Z", through the inspection zone within the inspector 12. The design of this transport system permits inspection of the parts at a high rate while restraining them against random lateral movements, rotation or slowdown during their translatory movement.

Figure 5:
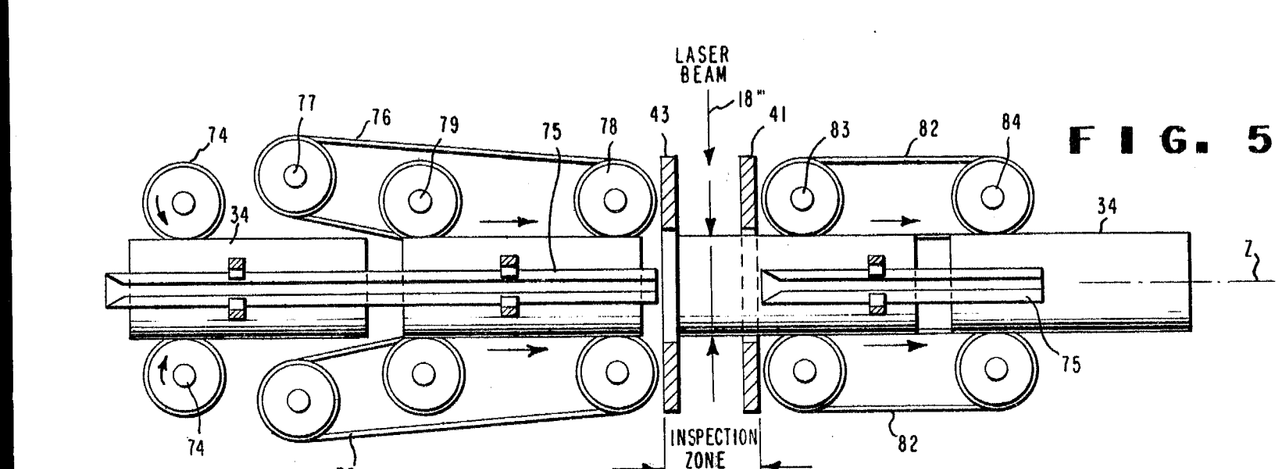
FIG. 5 is a diagrammatic representation of a typical transport system that may be employed to feed cylindrical articles through an inspection zone for inspection in accordance with this invention.

The transport mechanism is arranged to separate the parts longitudinally so that each set of individual inspections signals can be derived and associated with a corresponding discrete article. In the preferred construction of the transport mechanism, article separation is achieved by first gripping and feeding the articles at a lower uniformly velocity between a pair of diametrically opposed nip rolls 74, and then passing them through first and second pairs of parallel opposed feed belts 76 and 82, which are driven at a higher uniform velocity. As a result of this speed differential, the belts 76 feed the parts downwardly through the inspection zone and to the second pair of belts 82 in a uniform spaced apart relation as is seen in FIG. 5. Pairs of front linear guides 75 and back linear guides slotably engage and locate the parts in a plane at right angles to the common plane of engagement of the parts by the rolls 74 and the belts 76 and 82 respectively.

The height of the inspection zone, corresponding to the vertical gap between the belts 76 and 82, is less than the length of the smallest parts to be inspected, so that the parts are positively positioned during their passage through the inspection zone by spaced-apart locating means comprising the belts 76 and 82 and the guides 75. Thus, those articles which have the correct cylindrical form are centered on the feed axis 33 while irregular articles are laterally positioned according to their individual deformities. The upper belt 76 is mounted on pairs of drive pulleys 79 and pulleys 78 and tension adjusting pulleys 77, while the lower belts 82 are trained around corresponding drive pulleys 83, idler pulleys 84 and tension adjusting pulleys (not shown). These pulleys may be mounted upon a suitable frame that will permit adjustment of the opening to accommodate different sized articles. Similarly, linear guides 75 are spring loaded so that they automatically accommodate to the dimension of the particular articles being inspected.

In still another alternative embodiment of the invention, the articles may remain stationary and the inspection zone itself (FIG. 2) comprising primarily the "C" bracket 24, the laser 20, and the rotating drum 36 may be constructed as a unitary assembly and moved, in position, transversely to the axis 33, along the axis to scan the article from one longitudinal end to the other. In another alternative embodiment it is possible to substitute for the discrete planar mirrors of FIG. 3 a continuous parabolic or elliptical mirror suitably masked to obtained the desired signal outputs.

These and other alternative embodiments all permit the objectives of this invention to be achieved, that is, inspection of articles at a high rate of speed with a high selectivity, and greater than 100% of the inspection of the surface of these articles even though they be cylindrical.

I claim:

1. A method of optically inspecting the peripheral surface of an elongated generally cylindrical article having an axis comprising the steps of:

successively scanning said surface transversely of said axis with moving beams of light directed from each of a plurality of different circumferential locations, said beams of light lying in a plane sensing the intensity of light non-specularly reflected from said surface from each of said locations simultaneously at different axial locations on either side of said scanning position, said non-specularly reflected light being sensed simultaneously at a small angle relative to said plane of said light beams and at all circumferential positions about said axis, varying the position of said scanning along said axis by moving said article along said axis, and comparing variations in said reflected light intensity.

2. The method of claim 1 wherein said intensity variations are compared to a reference level.

3. A method of optically inspecting the peripheral surface of an elongated generally cylindrical article having an axis comprising the steps of:

successively scanning said surface transversely of said axis with moving beams of light directed from each of a plurality of different circumferential locations, said beams of light being in a plane, sensing the intensity of light non-specularly reflected from said surface from each of said locations, said non-specularly reflected light being sensed simultaneously at a small angle relative to said plane of said light beams and at all circumferential positions about said axis, varying the position of said scanning along said axis, and comparing variations in said reflected light intensity.

4. A method of optically inspecting the peripheral surface of an elongated generally cylindrical article having an axis comprising the steps of:

successively scanning said surface transversely of said axis with moving beams of light directed from each of a plurality of different circumferential locations, at least a portion of said scanning being by a single beam reflected from specular surfaces angularly positioned about said axis, said circumferential locations being five in number, sensing the intensity of light non-specularly reflected from said surface from each of said locations, varying the position of said scanning along said axis, and comparing variations in said reflected light intensity.

5. The method of claim 4 wherein one of said beams of light is direct from a single scanning source and the remaining beams of light are reflected beams from said single scanning source.

6. An optical inspecting apparatus for inspecting with a beam of radiation the surface of geometric characteristics of an elongated generally cylindrical article having an axis comprising, in combination:

a rotatable mirror drum of regular polygonal cross-section, means to direct said beam onto said drum for successively scanning said beam across said article in a plane transversely of said axis, a plurality of stationary specular surfaces disposed in said plane at different circumferential positions about said axis, each for reflecting said beam in said plane across said member surface from a different radial location, first annular sensing means positioned parallel to said plane, contiguous thereto, and about said axis for sensing radiation from said beam nonspecularly reflected from said member surface, and means for effecting relative movement along said axis between said scanning plane and said article.

7. The apparatus of claim 6 wherein said means for effecting movement translates said article along said axis.

8. The apparatus of claim 7 which also includes a second annular sensing means positioned contiguous and parallel to, but on the opposite side of, said plane from said first annular sensing means, thereby to sense low angle reflected radiation from said article.

9. The apparatus of claim 8 wherein said surfaces are n in number and are positioned angularly $2\pi/n+1$ radians apart about said axis to direct said beam both directly and by reflection across the entire circumference of said article.

10. The apparatus of claim 9 which also includes adder means for subtracting the outputs of said first and second sensing means.

11. The apparatus of claim 6 wherein said surfaces are n in number and are positioned angularly $2\pi/n+1$ radians apart about said axis to direct said beam both directly and by reflection across the entire circumference of said article.

12. The apparatus of claim 8 which also includes adder means for subtracting the outputs of said first and second sensing means.

13. The apparatus of claim 12 wherein said surfaces are n in number and are positioned angularly $2\pi/n+1$ radians apart about said axis to direct said beam both directly and by reflection across the entire circumference of said article.

14. The apparatus of claim 9 wherein said surfaces are four in number and are mounted on a C-shaped bracket.

* * * * *

UNITED STATES PATENT OFFICE
CERTIFICATE OF CORRECTION

PATENT NO. : 4,203,673
DATED : May 20, 1980
INVENTOR(S) : GERALD IRVING BUCKSON

It is certified that error appears in the above-identified patent and that said Letters Patent are hereby corrected as shown below:

Change assignee from "E. I. du Pont de Nemours and Company to --Remington Arms Company, Inc.--.

Signed and Sealed this

Nineteenth Day of May 1981

[SEAL]

Attest:

RENE D. TEGTMEYER

Attesting Officer     Acting Commissioner of Patents and Trademarks